United States Patent [19]

Schrader

[11] 4,394,496
[45] Jul. 19, 1983

[54] EPOXIDATION PRODUCTS OF 1,1,1-TRI-(HYDROXYPHENYL) ALKANES

[75] Inventor: Paul G. Schrader, Antioch, Calif.

[73] Assignee: The Dow Chemical Company, Midland, Mich.

[21] Appl. No.: 316,586

[22] Filed: Oct. 30, 1981

Related U.S. Application Data

[63] Continuation-in-part of Ser. No. 234,237, Feb. 13, 1981, abandoned, which is a continuation-in-part of Ser. No. 906,384, May 16, 1978, abandoned, which is a continuation-in-part of Ser. No. 646,730, Jan. 5, 1976, abandoned, which is a continuation-in-part of Ser. No. 173,259, Aug. 19, 1971, abandoned.

[51] Int. Cl.$^3$ .............................................. C08G 59/32
[52] U.S. Cl. .................................. 528/98; 528/112; 528/124; 549/517; 549/551; 549/559; 549/560
[58] Field of Search ............... 549/517, 551, 559, 560; 528/98

[56] References Cited

U.S. PATENT DOCUMENTS

| | | | |
|---|---|---|---|
| 2,857,362 | 10/1958 | Sheperd et al. | 260/47 |
| 2,965,611 | 12/1960 | Schwarzer | 260/47 |
| 3,687,897 | 8/1972 | Clarke | 260/59 |
| 3,787,451 | 1/1974 | Mah | 260/348 R |
| 3,789,053 | 1/1974 | Clarke | 260/47 EN |

FOREIGN PATENT DOCUMENTS

| | | |
|---|---|---|
| 240906 | 6/1960 | Australia . |
| 875811 | 8/1961 | United Kingdom . |
| 1155543 | 6/1969 | United Kingdom . |
| 1159530 | 7/1969 | United Kingdom . |

OTHER PUBLICATIONS

Dearborn et al., "Epoxy Resins from Bis, Tris, and Tetrakis-glycidyl Ethers, Ind. & Eng. Chem.", 45(12), 2715–2721, (1953).

*Primary Examiner*—Earl A. Nielsen
*Attorney, Agent, or Firm*—R. R. Stringham

[57] ABSTRACT

The invention comprises polyglycidyl ethers of tris(hydroxyphenyl)alkanes, their blends with other epoxy compounds and their cured products. The invention also comprises a process wherein the coupling reaction is carried out in the absence of coupling catalysts and solvents and the subsequent dehydrohalogenation is done in the presence of a methylethylketone/toluene mixture or an equivalent solvent. The epoxides of the invention have superior and unexpected high-temperature properties, without sacrificing other properties such as flex strength, flex modulus and the like.

33 Claims, No Drawings

EPOXIDATION PRODUCTS OF 1,1,1-TRI-(HYDROXYPHENYL) ALKANES

CROSS-REFERENCE TO RELATED APPLICATIONS

The present application is a continuation-in-part of my co-pending application Ser. No. 234,237, filed Feb. 13, 1981, now abandoned, which in turn is a continuation-in-part of application Ser. No. 906,384, filed May 16, 1978, now abandoned, which in turn is a continuation-in-part of application Ser. No. 646,730, filed Jan. 5, 1976, now abandoned, which in turn is a continuation-in-part of application Ser. No. 173,259, filed Aug. 19, 1971, now abandoned.

BACKGROUND OF THE INVENTION

Di-, tri- and tetra(hydroxy phenyl)alkanes have previously been reacted with compounds such as epichlorohydrin to form the glycidyl ethers thereof. These ethers have been cured to produce resins which were expected to possess good high-temperature properties, said properties being in large demand.

The feasibility of producing epoxides from such poly(hydroxy phenyl)alkanes is recognized in the art due to the availability of starting materials such as leucaurin.

Tris(4-hydroxyphenyl)methane, commonly known as leucaurin, has been prepared by the reduction of aurin with zinc dust and acetic acid. It (and isomers or homologs of it) may also be prepared by the condensation of a phenol with the appropriate hydroxy substituted aromatic ketone or aldehyde. For instance, tris(4-hydroxyphenyl)ethane is prepared by the reaction of phenol and 4-hydroxyacetophenone (see U.S. Pat. No. 3,579,542). One can prepare derivatives having substituents on the phenol-derived phenyl rings from the correspondingly substituted phenol reactant.

Derivatives having alkoxy substituents on the ketone- or aldehyde-derived phenyl ring may be prepared according to U.S. Pat. No. 3,787,451.

Dearborn et al. (*I.E.C.* 45, No. 12) reported the preparation of epoxides from polyfunctional phenols by a process wherein the phenol, epichlorohydrin ("epi") and caustic were mixed and heated, thereby coupling and dehydrohalogenating in a single operation. I have determined that the leucaurin epoxide prepared according to their method had an epoxy functionality of about 2 and (when cured) a relatively poor high-temperature performance (see Table 7 in Example 8 herein). Also see U.S. Pat. Nos. 2,857,362 and 2,863,852 (Dearborn et al.), which pertain to the above-reported research.

U.S. Pat. No. 2,965,611 (Schwarzer) teaches the epoxidation of tri- and tetra(hydroxyphenyl)alkanes wherein no more than two epoxyalkoxyphenyl groups are attached to the same carbon. Schwarzer's epoxidation method was similar to Dearborn's, except that the phenol-epi mixture was heated to reflux prior to the addition of aqueous caustic. However, he prepared an epoxide only from a tetrakis-compound.

British Pat. No. 875,811 (Neumann) discloses the use of solid, rather than aqueous, caustic in preparing the Schwarzer tris-epoxide by an otherwise similar method.

The advantages of epoxy resins for a wide variety of applications are well known but it has been necessary to use otherwise generally less tractable types of resins—most notably polyimides—for applications in which a Heat Distortion Temperature (HDT) in excess of about 315° C. is specified. To the best of the present inventor's knowledge, the highest HDT's reported for known epoxy resins are 257° C. (for the tetraglycidyl ether of 1,2,2,3-tetrakis(4-hydroxyphenol)propane, U.S. Pat. No. 2,965,611); 303° C. (for the triglycidyl ether of 1,2,2-tris(4-hydroxyphenyl)propane, British Pat. No. 875,811) and 315° C. (for "Epoxylite high temperature resins" manufactured by the Epoxylite Corporation and believed to be based on 1,1,2,2,-tetrakis(4-glycidyloxyphenyl)ethane). Of course, properties other than HDT, such as pot life, thermal stability, flexural strength, resistance to heat and moisture, resistance to chemicals and/or solvents and processability are also highly important. It is a balanced combination of high HDT and good performance in other regards that is essential to the commercial success of any resin. This combination has not really been realized and the teachings of the prior art fail to make obvious which, if any, possible resin structures can provide it.

OBJECTS OF THE INVENTION

The primary object of the present invention is to provide a family of epoxy resins having the combination of HDT's up to 350° C. with good or even superior performance in other regards, including processability.

Another object is to provide a novel process which is particularly suitable for the preparation of higher molecular weight, solid (oligomeric) epoxide products from 1,1,1-tri(hydroxyphenyl)alkanes but is also controllable to produce predominantly monomeric products.

A further object is to provide triglycidyl ethers of tri(hydroxyphenyl)alkanes—most notably of tris(4-hydroxyphenyl)methane—having epoxide equivalent weights very close to (or equal to) the theoretical values.

An additional object is to provide both monomeric and oligomeric epoxides of 1,1,1-triphenylalkanes in which the rings are each substituted with up to two hydroxyls.

Still other objects will be made apparent to those knowledgeable in the art by the following specification and claims.

SUMMARY OF THE INVENTION

The present invention provides monomeric and oligomeric polyglycidyl ethers of substituted or unsubstituted tri(hydroxyphenyl)alkanes in which all three hydroxyphenyl groups are attached to the same carbon. These ethers (hereinafter "epoxides", "epoxy" or "epoxidation products") are provided in near theoretical yield and conversion, together with an efficient method of preparing them, blends of them with other epoxy compounds and cured products derived from them, singularly or in combination with other epoxides.

More precisely, the present invention is the monomeric and/or oligomeric epoxidation product of a phenolic compound of the formula

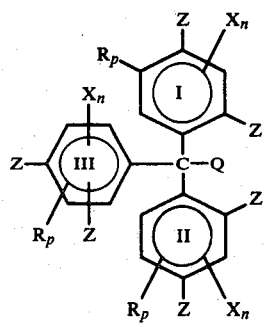

wherein:

Q is H or an alkyl group of from 1 to about 10 carbon atoms;

each R independently represents an alkyl group of from 1 to about 12 carbon atoms, phenyl or cycloalkyl of from 3 to about 6 carbon atoms;

each Z independently represents H or OH, with the proviso that at least one Z group on each of Rings I, II and III is OH;

each X independently represents bromo, chloro or nitro;

each p independently is 0, 1 or 2, each n independently is 0, 1, or 2, the sum of n+p for each ring being 0, 1, 2 or 3 when each Z is other than hydrogen, and an epihalohydrin of the formula:

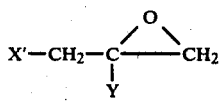

wherein X' is Cl or Br and Y is H or —CH₃;

said epoxidation product having an average epoxide functionality of from about 2.5 to about 6.0, or at least about 70% of theoretical for the number of available hydroxyls, whichever is greater.

Said monomeric epoxidation product preferably consists essentially of molecules of the formula

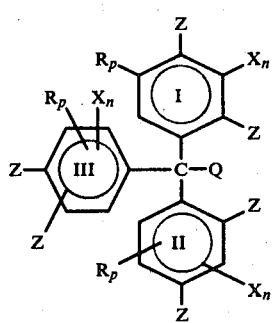

wherein

Q is H or an alkyl group of from 1 to about 10 carbon atoms;

each R independently represents an alkyl group of from 1 to about 12 carbon atoms, phenyl or cycloalkyl group of from 3 to about 6 carbon atoms; and each Z independently represents H or

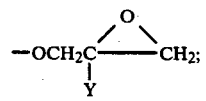

with the proviso that at least one Z on each of Rings I, II and III is

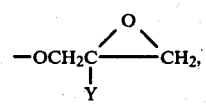

each Y independently represents H or methyl;

each X independently represents bromo, chloro or nitro;

each p independently is 0, 1 or 2, each n independently is 0, 1 or 2, and the sum of n+p for each ring being 0, 1, 2 or 3 when both Z groups are other than hydrogen.

The presently most preferred compositions are those derived from tri(hydroxyphenol)alkanes corresponding to the epoxides of the foregoing formula in which Q is H. Especially preferred are such products derived from 2,4',4''-trihydroxy(triphenylmethane).

Other epoxidation products comprising not only the monomeric epoxides but also oligomers, e.g., dimers, trimers, tetramers and some higher oligomers are formed under some conditions, e.g., from as little as 5 up to about 95 wt. %, of the product consisting of oligomers formed from the monomer via oxirane/—OH adduction during the epoxidation reaction. These oligomers can be exemplified by the leucaurin-deriveable products of the following Formula II (wherein, for purposes of illustration only, one Z group per ring and each Q and Y are H, and each n and p are zero):

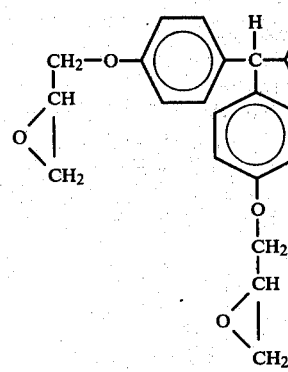
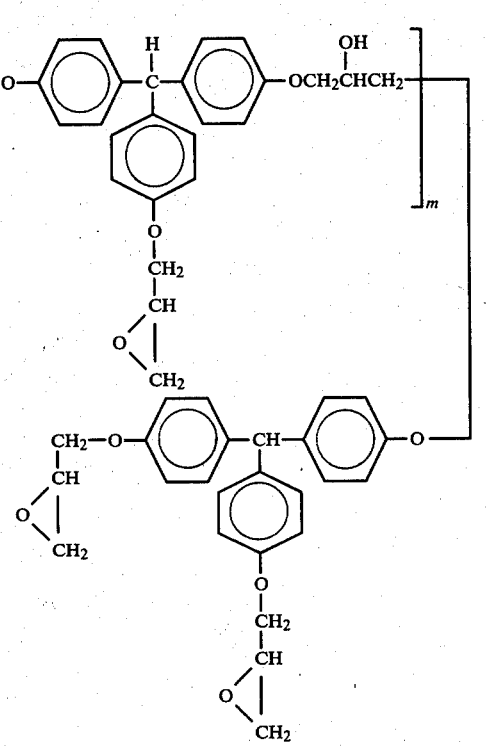

(II)

wherein m=0, 1 or 2. The $R_p$, $X_n$, Q, Z and Y groups can be present and have the same meaning as set forth above. Those skilled in the art will recognize that similar oligomers can be formed from other monomeric epoxides of Formula I as well. They will further recognize that small amounts of oligomers in which more than two of the epoxide groups in a single monomeric molecule have been reacted out with hydroxyl groups may be present in the epoxidation product.

DETAILED DESCRIPTION OF THE INVENTION

The above monomeric epoxides of the instant invention largely predominate in epoxidation products prepared by a process as follows:

1. A leucaurin-type phenolic compound, corresponding to the above formula A (where at least one Z group on each of the phenol-derived phenyl rings (Rings I and II) and the aldehyde- or ketone-derived phenyl ring (Ring III) is an OH group, the remaining Z groups on Rings I—III being hydroxy or hydrogen) is reacted with from about 5 to 20 or more moles of an epihalohydrin per equivalent of phenolic hydroxyl, the epihalohydrin being of the formula

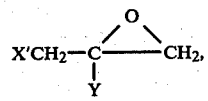

wherein X' is Cl or Br and Y is H or CH₃. The reaction is carried out in the presence of a coupling catalyst, such as benzyltrimethylammonium chloride, the reactants being heated to a temperature of from about 60° to 150° C., preferably at reflux, for at least about 30 minutes, usually from about 30 minutes to about two and one-half hours, and preferably for about one hour.

2. At the end of said period, the mixture is cooled to from about 20° to 70° C. and at least about one equivalent of caustic is added per hydroxyl equivalent. The reaction mixture is then agitated, usually by stirring, and heated for from about one-half to about three hours. The resulting "epoxidation" product (polyglycidylether) has an average epoxide functionality (depending upon the completeness of the reaction) of from about 2.5 (where Q is H, n and p are zero and each of Rings I, II and III of the representative formula have only one epoxide group) to about 6.0, preferably from about 2.5 to about 5.0, or at least 70% of theoretical for the number of available hydroxyls on the starting triphenolic precursor material, whichever is greater. For the preferred monomeric products, the theoretical epoxide functionality would be 3.0 where one Z group per ring is always H, and 6.0 wherein each ring has two available hydroxyls on the phenolic starting material and each are converted to an epoxy group.

By reducing the epihalohydrin to phenolic hydroxyl ratio in the foregoing process, substantial amounts of oligomers may be co-formed with the monomeric epoxides. However, a different epoxidation process, described subsequently herein, is better suited for production of oligomers (but can also be carried out at sufficiently high reactant ratios to yield products having high monomeric epoxide contants). Said process is novel and is part of the present invention.

For oligomeric epoxidation products, the theoretical maximum epoxide functionality, wherein the starting tri-phenolic precursor has only one hydroxyl group per ring, would be 4.0 where m=0 (dimer), and 6.0 where m=2 (tetramer). Where the triphenolic precursor has two available hydroxyls per ring and each is converted to an epoxy group, the maximum theoretical epoxide functionality is higher, e.g., 10.0 where m=0 up to 18.0 where m=2. However, such oligomer-containing products are considered to be within the scope of the invention as long as the resulting product has an average epoxide functionality of at least 70% of the theoretical for the number of available hydroxyls on the starting material, i.e., when each Z is a hydroxyl, the epoxide functionality is at least $0.7 \times 6 = 4.2$.

The products of the invention are viscous liquids or solids at room temperature, the monomers usually being very fluid at about 50° C., while the oligomers have a softening point of about 80°–95° C. or higher. As evidenced by the average EEW's and molecular weights actually found for the stripped products, they contain only relatively small amounts of by-products; most notably, in production of predominantly oligomeric products by the earlier referred-to novel process.

By inspection of the foregoing Formula II, it is apparent that the molecular weight of such an oligomer is equal to the sum of the molecular weights of one fully epoxidized polyol molecule and $m+1$ polyolmolecules in which all but one of the hydroxyls has been converted to a glycidyl ether group. That is, $M_o = (M_p - N + NM_G) + (m+1)$ $[M_p - (N-1) + (N-1)M_G]$; $M_o$, $M_p$ and $M_G$ being the molecular weights respectively of the oligomer, the polyphenol and a glycidyl group of the formula

(Y being defined as in Formula B), and N being the number of available hydroxyls in the polyphenol.

It is also apparent that the epoxide functionality for such an oligomer may be expressed as $f_E = m(N-2) + 2(N-1)$.

Accordingly, the following relationship can be derived from the two preceding ones:

$$f_E = \frac{(N-2)(M_o - 2M_p - (2N-1)M_G + 2N - 1)}{M_p + (N-1)(M_G - 1)} + 2(N-1) \quad (1)$$

The actual, average epoxide functionality for a given product—or fraction thereof separated by preparative GPC (Gel Permeation Chromatography)—of course can be taken as the ratio of the average molecular weight to the epoxide equivalent weight (EEW), both of which can be experimentally determined. However, for the purpose of defining the predominantly oligomeric products of the present invention, relationship (1) may be utilized to estimate the maximum epoxide functionality that such a product of a known average molecular weight may have. (And, of course, the maximum value of m can then also be estimated.) If the monomeric epoxides are first largely eliminated (as by GPC), the molecular weight (used as $M_o$) will be more representative of the oligomeric portion of the product and a higher value of $f_E$ will be obtained.

In the broadest definition of the epoxidation products of the invention, given earlier herein, reference is made to the product having an average epoxide functionality of from about 2.5 to about 6, or at least about 70% of theoretical for the number of available hydroxyls, whichever is greater. As applied to those products comprising oligomers, the epoxide functionality can exceed 100% of the theoretical value for the monomeric product—but cannot exceed the value of $f_E$ calculated from expression (1).

The polyepoxides thus prepared may be admixed prior to curing with other epoxides to result in a blend with desirable properties. Usually, such other epoxides are employed in amounts of from about 5 to about 95 weight percent. Examples include mono-functional reactive diluents, such as phenyl glycidyl ether, allyl glycidyl ether, butyl glycidyl ether, cyclohexene monoxide, and the like; alkylene oxides, such as butylene oxide, propylene oxide, octylene oxide, and the like. Polyfunctional epoxides are also suitable, such as epoxy novolacs, liquid and solid diglycidyl ethers of dihydroxy compounds, butadiene dioxide, 4,4'-isopropylidene diphenol, diglycidyl ether, cyclopentadiene dioxide, vinyl cyclohexene dioxide, bis(2,3-epoxycyclopentyl)ether, diglycidyl phthalate, diglycidyl aniline, tris epoxides from aminophenols and epi, and the like. Mixtures of the above are also suitable. U.S. Pat. No. 2,935,488 (Phillips et al., 1960), for example, exemplifies mixtures of epoxies suitable herein. The polyepoxides of Formula I or II, alone or in combination with other resins, may then be cured under typical curing conditions with known catalysts, such as polyalkylene amines, aromatic diamines, anhydrides, melamine/formaldehyde resins and the like.

The resins so produced have the properties generally required for epoxides to be employed in such uses as potting, encapsulation, high performance coatings and foams, casting, tooling, high temperature wire coatings, caulking compounds, fiber-resin composites, laminates, adhesives, molding compounds, and the like. However, they are also much more resistant to heat distortion than the epoxies conventionally employed in such applications.

The leucaurin-type phenolics which are the precursors to the epoxies of the instant invention are generally prepared by condensing an aromatic aldehyde or ketone, such as hydroxybenzaldehydes or hydroxyalkanophenones, with an excess, preferably a large excess, of a substituted or unsubstituted phenol.

The reactant mixture is stirred, often with heating, and with introduction of a strong acid, such as $H_2SO_4$, HCl or HBr, as catalyst. The ensuing reaction is exothermic and after the exotherm subsides the predetermined reaction temperature is established and continued until the reaction reaches substantial completion. Isolation of the product is carried out by conventional techniques and procedures.

Preferred epoxides of the present invention include various species corresponding to the above Formula I. In one such preferred embodiment, n and p are zero and each of the Z groups in the para positions on the rings (I, II, or III) they are attached to is an

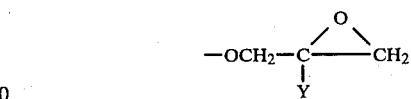

group, all of the other Z groups being hydrogen. In further embodiments, epoxide products wherein n and/or p is zero are preferred. In a further preferred embodiment, one Z group of Ring III is hydrogen. Another preferred class of epoxides are those of Formula I wherein n and p are zero and one Z of Ring III is hydrogen. In another such embodiment, epoxides wherein n is zero, one of the Z groups on Ring III is hydrogen and Q is hydrogen are preferred. In an additional embodiment, epoxide products wherein each Z is

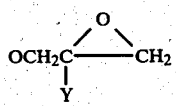

are preferred. In yet another embodiment, epoxide products having an average epoxide functionality of from about 2.8 to about 4.5 are preferred. The most preferred epoxy products of this invention consist at least predominantly of 2,4′,4″tri((2,3-epoxypropoxy)-phenyl)methane or tris(4(2,3-epoxypropoxy)-phenyl)methane. These products have an epoxy equivalent weight of from about 153 to 170, an average epoxide functionality of about 2.8 to about 3.2 and a viscosity of from about 8500 to about 30,000 cps or more - preferably from about 8500 to about 18,000 cps, at 50° C. (EEW of the pure tris-epoxide=153.7)

As indicated in the above reaction description, the tri(polyhydroxyphenyl)alkanes suitable herein for epoxidation are those of Formula A wherein the phenol-derived phenyl rings (Rings I and II) have hydroxy groups in the ortho and/or para positions. However, the aldehyde- or ketone-derived ring (III) also can have up to two hydroxy substituents which can be in the ortho, meta or para position(s). Each of Rings I, II and III can be further substituted in available ring positions with R or X groups as defined.

By use of substituted phenol and aldehyde or ketone reactants, or by the condensation of unsubstituted reactants to the three ring structure followed by introduction of desired substituents, leucaurin-type polyphenols with a wide range of substituents can be prepared.

In selecting the appropriate reactants to prepare the precursors, which subsequently are "epoxidized" to obtain the products of the present invention, it will be recognized by those skilled in the art that the presence of certain substituents, notably meta-directing groups, may tend to inhibit the condensation of phenols and aldehydes or ketones to leucaurin-like materials. In such instances, those skilled in the art will also recognize that condensation of the phenol and aldehyde reactants can be carried out first and the resulting product subsequently substituted. In such operations, it is desired that such substitution process be carried out prior to epoxidation since the oxirane rings may be vulnerable to opening during such processes, thereby destroying their functionality. It is especially desired that the halo and nitro substituents on the phenol-derived Rings I and II be substituted thereon after condensation with the aldehyde or ketone reactant. While numerous substituted phenol reactants bearing halo and nitro substituents are available, they often tend to inhibit condensation with aldehyde or ketone reactant to form the leucaurin-type precursors, although halo- or nitro-substituted aldehyde or ketone reactants (e.g., Ring III substituents) can be utilized as they do not appear to inhibit the condensation reaction.

Those skilled in the art will further recognize how the reactivity of the reactants employed will vary, depending upon the nature, locations, and steric effects of the substituents on the ring. It will also be apparent to the skilled artisan that ortho-substituted phenols have an open, active para position which usually yield, upon condensation with the aldehyde or ketone reactant, a substantially pure crystalline precursor which is readily recovered. Para substituted phenols having open, active ortho positions for the condensation reaction usually result in a precursor consisting of mixed polyphenol isomers and some higher molecular weight products which may not readily separate as a solid material. In these instances, an acetic acid solution of the precursor product can be poured into water to separate the product plus resin, which can then be washed in a sodium bicarbonate solution and then water. The mixture is then stripped of water and solvent to obtain the polyphenols product as a solid material.

Thus, substituted or unsubstituted polyphenol having ortho or para hydroxy groups in Rings I and II of the above formula can be prepared by utilizing phenol reactants such as, for example, phenol, substituted phenols having alkyl, cycloalkyl or phenyl substituents, e.g., o-, m- and p-cresol, 2,6-dimethylphenol, 2,6-dipropylphenol, 2,6-didodecylphenyl, 2,6-di-tert-butylphenol, 2,6-diphenylphenol, 2,6-dicyclopropylphenol, 2,6-dicyclohexylphenol, 2,3-dimethylphenol, 2-dodecylphenol, 2-cyclohexylphenol, 3,5-dimethylphenol, p-tert-butylphenol, 3,5-di-tert-butylphenol, 4-dodecylphenol, 2,4-didodecylphenol, 4-pentylphenol, 2,4-diphenylphenol, 3,5-dimethylphenol, 4-cyclohexylphenol, 2,4-dicyclohexylphenol, and the like.

In those instances where substituted or unsubstituted polyphenols having ortho- and para-hydroxy groups in each of Rings I and II are desired, reactants such as, for example, resorcinol, 2-methyl resorcinol, 5-methyl resorcinol, 4-n-hexyl resorcinol, p-dodecyl resorcinol, 5-cyclohexyl resorcinol, 1,3-dihydroxy-2,4-dimethylbenzene, 1,3-dihydroxy-2,5-dimethylbenzene, 1,3-dihydroxy-2,4-dinitrobenzene, 1,3-dihydroxy-2-nitrobenzene, 1,3-dihydroxy-4-n-butylbenzene, 1,3-dihydroxy-5-pentylbenzene, 1,3-dihydroxy-5-propylbenzene, 1,3-dihydroxy-2,4,5-trimethylbenzene, 4-phenyl resorcinol, 1,3-dihydroxy-2,5-didodecylbenzene, and the like may be employed.

Other reactants to the foregoing which can be used to obtain Rings I and II of the precursors are also known and are available or can be prepared by known methods by those skilled in the art.

Halogenated or nitrated phenol reactants are available, e.g., 2,6-dichlorophenol, 2-nitrophenol, 2-bromophenol, 2,4-dichlorophenol, 2,5-dichlorophenol, 2,6-dinitrophenol, 3-bromo-5-chlorophenol, 2-chloro-5-nitrophenol, and the like; however, it is preferred that such halo or nitro substituents be introduced after condensation of the phenol and aldehyde reactants are set forth hereinabove.

With respect to the aldehyde- or ketone-derived portion of the polyphenol (i.e., Ring III in formula A above wherein one or both of the Z groups are hydroxy groups), substituted or unsubstituted aldehydes or ketones having one to two hydroxy groups in the ortho-, meta- or para-positions of Ring III can be utilized. Such polyphenols can be obtained by using reactants such as, for example, salicylaldehyde (2-hydroxybenzaldehyde), 2-hydroxyacetophenone, 2-hydroxybutyrophenone, 2-hydroxy-3-nitrobenzaldehyde, 2-hydroxy-5-methylacetophenone, 4-chloro-2-hydroxybenzaldehyde, 2-hydroxypropiophenone, 3-hydroxybenzaldehyde, 3-hydroxy-4-nitrobenaldehyde, 2,4-dichloro-3-hydroxybenzaldehyde, 4-bromo-3-hydroxybenzaldehyde, 2-chloro-3-hydroxybenzaldehyde, 3-hydroxy-4-nitrobenzaldehyde, 4-hydroxyacetophenone, 4-hydroxybenzaldehyde, 3-bromo-4-hydroxybenzaldehyde, 3,5-dichloro-4-hydroxybenzaldehyde, 4-hydroxy-2-methylacetophenone, 4-hydroxy-3-methylacetophenone, 4-hydroxy-2-nitrobenzaldehyde, 4-hydroxy-3-nitrobenzaldehyde, 4-(p-hydroxyphenyl)-2-butenone, and the like.

Those skilled in the art will recognize that other precursor materials bearing desired R and X substituents as defined can be prepared by using reactants similar to those illustrated above for Rings I–II and for Ring III. These reactants are readily available or can be prepared by those skilled in the art using known or analogous methods taught in the literature.

The halogenation and nitration reactions employed to substitute Rings I and II after the condensation reaction to form the leucaurin-type polyphenol has taken place, but before the epoxidation reaction is carried out, are typical and readily apparent to those skilled in the art. Generally, if the precursor polyphenol is to be halogenated, it is dissolved in an appropriate carrier medium, for example, glacial acetic acid, and the halogen added thereto (chlorine by sparging the desired amount of gas into the reaction mixture, or bromine by addition of the liquid) at ambient temperatures with stirring. Following the addition of the desired amount of halogen (for example, about 71 grams of chlorine are needed to add an average of 6 chlorine groups to leucaurin), the reaction mixture is mixed with water and the resulting mixture filtered. The filter cake thus obtained, representing the desired product, is washed with water until acid free and dried. In nitration procedures, similar operations are followed with the nitrating agent, e.g., concentrated nitric acid, usually being mixed with a portion of the carrier medium prior to addition to the leucaurin-type polyphenol. The substituted polyphenol can then be epoxidized (—OH groups converted to glycidyl ether groups) as set forth herein.

In the method best suited for making monomeric tris (etc.) epoxides, the first step is to cause the tri(hydroxyphenyl)alkane of Formula I to couple with an epihalohydrin in the presence of a coupling catalyst under the conditions previously given. Suitable catalysts include benzyltrimethylammonium halides, such as the chloride; tertiary amines, such as benzyldimethylamine, triethylamine, N,N,N',N'-tetramethyl ethylenediamine and the like; N-methylmorpholine; triphenylphosphonium halides, such as the iodide, bromide or chloride; triphenylethylphosphonium diethyl phosphate and other corresponding ionic salts including phosphonates, acetates, nitrates and the like. The preferred catalyst is benzyltrimethylammonium chloride (BTMAC).

After a sufficient time has elapsed to insure the desired degree of coupling of "epi" groups to hydroxyls, the reaction mixture is cooled to the afore specified temperature range. Dehydrohalogenation—the second step—is then brought about by the use of a base, such as NaOH, NaOH in saturated $Na_2CO_3$ solution, sodium aluminate, or the like. 3N NaOH is suitable, as is 30–50% NaOH added slowly to the solution with azeotropic removal of $H_2O$. One could also use 20% alcoholic KOH as reflux. 3N NaOH in saturated $Na_2CO_3$ is preferred.

The epihalohydrin with which the phenols are converted to their corresponding glycidyl ethers is most commonly epichlorohydrin. However, epibromohydrin, 1-chloro-2,3-epoxy-2-methylpropane and the like are also suitable.

In more detail, the preceding process is carried out by placing the polyphenol (preferably 4,4',4''- or 2,4',4''tri(hydroxyphenyl)methane, an epihalohydrin (preferably epichlorohydrin) and a condensation catalyst in a suitable flask equipped with a stirrer, thermometer and reflux condenser. The reaction mixture is then heated to reflux for about one hour. Thereafter, the flask is cooled to about 50° C., such as in a water bath, and, while maintaining that temperature, aqueous caustic in saturated $Na_2CO_3$ is added with stirring. At least one equivalent of caustic per equivalent of phenolic hydroxyl should be utilized, and it is preferred to use a slight excess over the stoichiometric amount.

At the end of an hour, during which the caustic addition is completed and heating and stirring are continued, the resulting mixture is permitted to segregate into organic and aqueous phases, and the aqueous phase removed. The remaining organic phase is then returned to the water bath, heated to 50° C. and stirring is continued while sodium hydroxide in saturated aqueous sodium carbonate solution is again added.

Heating and stirring are then continued at 50° C. for another hour, at the end of which time the aqueous phase is again removed. The resulting organic phase is washed once with water made slightly acid with acetic acid, and washed thereafter with water alone until the eluent is neutral to pH paper. If desired, the wash water may contain some sodium chloride to diminish the tendency of water to emulsify in the organic phase. Upon completion of water-washing, the resulting organic material is distilled off under sub-atmospheric pressure to remove traces of water and unreacted epichlorohydrin. As a result of these procedures there is obtained, for example, an epoxidized derivative of leucaurin which has molecular and epoxy eqivalent weights close to theoretical.

The novel procedure best adapted for making oligomeric products (Formula II) is generally described in the paragraph following Example 10 herein and is exemplified in detail in Example 11.

The polyepoxides of this invention may be blended with various other epoxides as is discussed above. For instance, they may be admixed with epoxy novolac resins to give a blend with a lower viscosity than that of the novolac alone, without sacrificing functionality and, consequently, with substantial retention of the physical and chemical properties of the cured epoxides of this invention. Likewise, these polyepoxides can be blended with liquid and solid diglycidyl ethers of dihydroxy compounds to slightly increase the cross-linking density of the cured product. By such blends it is possible to adjust the properties of a resin to those desired, generally higher service temperature in the cured product, without imposing any fabrication difficulties. The flexibility of this concept is exemplified in that the blends can be achieved by mixing the polyepoxides before curing or by blending the phenolic reactants before epoxidation. The possible combinations are innumerable. It has been found that utilizing as little as 5 wt. % of the epoxides of this invention with the above epoxides enhances their high temperature service.

The polyepoxides of the invention, as defined in Formulas I and II herein, are generally useful in the same areas as other epoxy resins, as outlined above.

The polyepoxides produced according to the teachings herein may be cured by typical agents under known conditions. It has been found that the following curing agents are quite suitable: methylene dianiline, m-phenylenediamine, and mixtures thereof; o- and p-phenylenediamines; benzidine; diaminodiphenylsulfone; 2,6-diaminopyridine; benzyldimethylamine; tetramethylethylenediamine; N-methylmorpholine; diethylene triamine; triethylenediamine; tetramethylguanidine; dicyandiamide; diemthylethanolamine; diethanolamine; trialkylamines, such as triethylamine, tripropylamine and tributylamine; 4-picoline; and the like. Also suitable are $BF_3$ complexes, such as $BF_3$ monoethylamine; borates, such as tricresyl borate; anhydrides, such as Nadic methyl anhydride, hexahydrophthalic anhydride, dodecenyl succinic anhydride, succinic anhydride, maleic anhydride, glutaric anhydride, pyromellitic dianhydride, trimellitic anhydride, tetrahydrophthalic anhydride, chlorendic anhydride, polysebacic polyanhydrides, polysulfides, polyazalaic anhydride, phthalic anhydrides, benzophenonetetracarboxylic acid dianhydride, cyclopentanetetracarboxylic acid dianhydride, and the like.

All of these curing agents can be employed with the leucaurin epoxides of this invention over a wide range of temperatures depending upon the properties desired and the curing agent used. One could use, for instance, 2 hours at 120° for a very moderate cure of the aromatic amines, tertiary amines, $BF_3$ complexes, borates, and the readily soluble or lower melting anhydrides. For optimum properties, which would most likely be desired when the tris(4-hydroxyphenyl)methane epoxide is being used, step-curing is most suitable, such as 16 hours at 85° C. plus 16 hours at 160° C., or 16 hours at 85° C. plus 16 hours at 160° C. plus 4 hours at 230° C. The shortest possible curing times are, of course, desirable and very high heat distortion temperatures (greater than 266° C.) can be achieved by curing 2 hours at 230° C. with such curing agents as methylene dianiline, meta-phenylenediamine, benzidine, diaminodiphenylsulfone, $BF_3$ complexes, maleic anhdride-trimellitic anhydride mixutes, maleic anhydride-pyromellitic anhydride mixtures, hexahydrophthalic anhydride-trimellitic or pyromellitic anhydride mixtures, phthalic anhydride mixed with trimellitic, or pyromellitic anhydride. Other anhydrides, such as cyclopentanetetracarboxylic acid dianhydride or benzophenonetetracarboxylic acid dianhydride mixed with maleic, phthalic, or hexahydrophthalic anhydrides, can also be used. Or, the high melting anhydrides can be used alone if they are milled into the resin to achieve complete dispersion.

Because of the outstanding heat distortion temperature and heat resistance of the cured epoxides of this invention, as manifested by a markedly increased service life at elevated temperatures, as well as other superior properties, these epoxides are suitable for use in many specialized fields of application.

In the area of fiberglass reinforced epoxies, they find application in high temperature ablative heat shields and nose cones as well as rocket motor cases and thrust chambers. Other uses are in laminates requiring high hot strength such as printed circuit boards. Since the cured products have outstanding chemical and solvent resistance, they can be used in epoxy-fiberglass pipe which will also have higher hot strengths than possible before. This is also true of pressure spheres and tanks requiring chemical, solvent and/or heat resistance. Hoods, stacks, and support members of epoxy/glass requiring greater acid, caustic, or solvent resistance are other possibilities.

The polyepoxides may also be used in structural composites with carbon fiber, boron fiber or glass fiber for aircraft for which more heat resistant components are now required.

In the electrical field these compositions, with proper curing agents, give cured formulations with higher heat resistance and hot strength than available before, low dielectric constants, high resistivity, low electrical loss, and superior arcing and tracking resistance.

Coatings based on or utilizing these new epoxies achieve greater chemical, heat, or solvent resistance. This is true for non-solvent coatings as well as for coatings based on fatty acid esters such as tung, dehydrated castor, or linseed.

These epoxies are also an excellent base for the more recently developed epoxy acrylate or other highly chemical resistant vinyl ester resins.

High temperature adhesives is an area in which the compounds of this invention are especially useful.

The following examples are for purposes of illustration and are not to be construed as limiting the present invention in a manner inconsistent with the claims appended to this specification.

SPECIFIC EMBODIMENTS

Example 1

Tris(4-hydroxyphenyl)methane, commonly known as leucaurin, was prepared in order to demonstrate at least one method for preparing the precursors to the polyepoxides of this invention.

Into a 3-necked flask equipped with a stirrer, thermometer and reflux condenser, was placed 122 grams of p-hydroxy benzaldehyde (1 gram mole) and 1410 grams of USP phenol (15 gram moles). The flask was placed over a 40° C. water bath and vigorous stirring begun. Anhydrous HCl was slowly bubbled into the mixture. The water bath cooled the reaction mixture as the resulting exotherm began to elevate the mixture's temperature, the maximum reaching about 44° C.

After the exotherm subsided, anhydrous HCl was bubbled in for about 6 hours with stirring, the mixture being maintained at 40° C. by the water bath. At the end of this period, the reaction mixture was allowed to stand overnight at room temperature.

The resulting mixture was washed twice with water, and then distilled under vacuum to remove most of the phenol. The remaining phenol was removed by flashing off with steam. Distillation was continued until all water had been removed.

There resulted a dark pink crystalline mass having only traces of resin. Product weight was 290 grams, which is 99% of theoretical.

Under similar reaction conditions, other precursors to the polyepoxides of the invention have been prepared. Table 1 below sets out the reactants and catalysts used. Reaction conditions and product work-ups are generally as described above. In Product C, the trihydroxy designations 2,4′,4″ indicate the positions of the hydroxy groups on Rings I, II and III, respectively, of the above formula (I). The same designations are used throughout the following examples.

TABLE 1

| No. | Reactant | Reactant | Catalyst | Product |
|---|---|---|---|---|
| A. | Phenol | 4-Hydroxyaceto- | Anhyd. HCl + thio- | 1,1,1-tris (p-hydroxyphenyl)ethane |

TABLE 1-continued

| No. | Reactant | Reactant | Catalyst | Product |
|---|---|---|---|---|
| B. | Phenol | phenone 4-Hydroxyoctano-phenone | glycolic Acid Anhyd. HCl + thio-glycolic Acid | 1,1,1-tris (p-hydroxyphenyl)octane |
| C. | p-Cresol | p-Hydroxybenz-aldehyde | Glacial Acetic Acid + $H_2SO_4$ | 2,2',4''-trihydroxy-5,5'-dimethyl-triphenylmethane |
| D. | 2-t-butylphenol | p-Hydroxybenz-aldehyde | Glacial Acetic Acid + $H_2SO_4$ | 4,4',4''-trihydroxy-3,3'-t-butyl-triphenylmethane |
| E. | Mixture of 4-octyl- and 4-dodecylphenol | p-Hydroxybenz-aldehyde | Glacial Acetic Acid + $H_2SO_4$ | 2,2',4''-trihydroxy-(mixture of 5,5'-didodecyl, dioctyl, and 5-octyl-5'-dodecyl)-triphenylmethane |
| F. | 4-n-hexyl-resorcinol | p-Hydroxybenz-aldehyde | $Z_nCl_2$ | 2,2',4,4',4''-pentahydroxy-5,5'-di-n-hexyl-triphenylmethane |
| G. | 4-cyclohexyl-resorcinol | p-Hydroxybenz-aldehyde | " | 2,2',4,4',4''-pentahydroxy-5,5'-dicyclohexyltriphenylmethane |
| H. | 4-dodecyl-resorcinol | p-Hydroxybenz-aldehyde | " | 2,2',4,4',4''-pentahydroxy-5,5'-didodecyltriphenylmethane |

EXAMPLE 2

The following example pertains to the preparation of dinitro leucaurin. Halogenated species may be prepared by analogous methods.

30 Grams of leucaurin was dissolved in 700 ml. of glacial acetic acid in a three-liter flask. 15 ml. of conc. $HNO_3$ in 85 ml. of glacial acetic acid was then slowly added, at a temperature of about 24° C., to the leucaurin. The resulting exotherm raised the flask contents to 28° C.

The reaction mixture was allowed to stand overnight, and then was poured into 1800 ml. of $H_2O$. The resulting precipitate was filtered and washed with water. The product, which was a bright yellow powder, weighed 35.5 grams, 90.5% of theoretical for dinitro leucaurin. It was found to contain 7.9% nitrogen, theoretical for dinitro leucaurin being 7.33%.

In similar operations, pentachloro-tris(4-hydroxyphenyl)methane was obtained by sparging sufficient amounts of chlorine gas through the leucaurin solution. The product was "epoxidized" as in the following Example 3 to obtain the trisepoxide product, which had an epoxy equivalent weight of 220 (theory 208) and a heat distortion temperature of 212° C.

EXAMPLE 3

The trisepoxide of leucaurin was prepared as follows: into a flask fitted with a stirrer, thermometer and reflux condenser was placed 290 grams (3 equivalents) of leucaurin, 2780 grams (30 moles) of epichlorohydrin and 2.9 grams of a 60 percent solution of benzyltrimethylammonium chloride (1% of the trisphenol). The flask was heated, with stirring, to reflux (119° C.) for one hour. After cooling, it was placed in a 50° C. water bath and 1000 milliliters of 3 molar NaOH in saturated $Na_2CO_3$ added (1 equivalent NaOH per equivalent of trisphenol). The mixture was stirred and heated to 50° C. for one hour. The spent NaOH was separated and the epichlorohydrin solution returned to the flask, heated in a 50° C. water bath and treated again with 500 milliliters of 3 molar NaOH-saturated $Na_2CO_3$ solution for one hour. The spent NaOH solution was again separated. The reaction mix was washed with dilute aqueous acetic acid, then with water until neutral to litmus paper. The water and epichlorohydrin were distilled away under vacuum.

The resulting resin had a color rating of 10 on the Gardner scale, an epoxy equivalent weight of 158 (theoretical 153), an average epoxide functionality of 3.1, a viscosity of 8,800 centipoises at 50° C. and a molecular weight of 490 (theoretical 463).

EXAMPLE 4

The trisepoxide of Example 3 was mixed with various curing agents, shaped into test specimens and cured. The pertinent data and results are in Table 2 below:

TABLE 2

| No. | Curing Agent | Parts/ Curing Agent/ 100 Parts of Resin | Cure Schedule | Barcol Hardness | Heat Distortion Temperature - °C. |
|---|---|---|---|---|---|
| 1. | BF3MEA | 3.0 | 16 hours @ 150° C. | 48 | 266* |
| 2. | DETA | 11.8 | 16 hours @ 180° C. | — | 263 |
| 3. | MXDA | 19.8 | 16 hours @ 160° C. | 42 | 221 |
| 4. | DADS | 35.6 | 16 hours @ 232° C. | 39 | 266 |
| 5. | BF3MEA | 3.0 | 2 hours @ 232° C. | 47 | 266 |
| 6. | DADS | 35.6 | 2 hours @ 232° C. | 45 | 266 |

*Upper limit of equipment (ASTM D648-56 used throughout)
BF3MEA — Boron Trifluoride Monoethylamine
DETA — Diethylenetriamine
MXDA — Meta-Xylylenediamine
DADS — Diaminodiphenylsulfone The same trisepoxide was also cured with mixtures of curing agents for 2 hours at 93° C. and then for 15 hours at 232° C. The curing agents used and the results are in Table 3:

TABLE 3

| No. | First Curing Agent | Parts Curing Agent/ 100 Parts of Resin | Second Curing Agent | Parts Curing Agent/100 Parts of Resin | Barcol Hardness | Heat Distortion Temperature - °C. |
|---|---|---|---|---|---|---|
| 7. | NMA | 92.0 | DMP 30 | 2.0 | 44 | 262 |
| 8. | TMA | 3.3 | MA | 38.6 | 49 | 266 |
| 9. | " | 0.86 | " | 45.7 | 49 | " |
| 10. | " | 8.0 | " | 24.0 | 46 | " |
| 11. | PMDA | 1.3 | " | 45.7 | 50 | " |
| 12. | " | 13.3 | " | 24.0 | 43 | " |
| 13. | " | 5.3 | " | 38.6 | 45 | " |

NMA — Nadic Methyl Anhydride
TMA — Trimellitic Anhydride
PMDA — Pyromellitic Dianhydride
DMP 30 — Tris(dimethylaminomethyl)phenol
MA — Maleic Anhydride

EXAMPLE 5

In a manner similar to the above examples, polyepoxides of a number of tri(hydroxyphenyl)alkanes were prepared, mixed with the stoichiometric amount of methylene dianiline cured at 100° C. for 2 hours and 180° C. for 18 hours, and tested. Flex strength and modulus throughout were determined by ASTM method D790-66. The results are in Table 4 below:

TABLE 4

| No. | Polyepoxide Of | EEW Calculated | EEW Found | HDT °C. | Barcol Hardness | FLEX Strength(psi) | FLEXURAL Modulus(psi) |
|---|---|---|---|---|---|---|---|
| 1. | 4,4',4''-trihydroxy-2,2'-dimethyl-TPM | 162.7 | 170 | 221 | 45 | 11,300 | 444,000 |
| 2. | 4,4',4''-trihydroxy-3,3'-dimethyl-TPM | 162.7 | 178 | 233 | 52 | 12,100 | 454,000 |
| 3. | 2,2',4''-trihydroxy-5,5'-dimethyl-TPM | 162.7 | 172 | 228 | 44 | 16,600 | 469,000 |
| 4. | 4,4',4'-trihydroxy-3,3'-diphenyl-TPM | 204.1 | 212 | 201 | 47 | 19,000 | 530,000 |
| 5. | 4,4',4''-trihydroxy-3,3'-dicyclohexyl-TPM | 208.2 | 218 | 208 | 48 | 15,100 | 411,000 |
| 6. | 2,2',4,4',4''-pentahydroxy TPM | 120.9 | 134 | 266 | 64 | 6,700 | 410,000 |
| 7. | 2,2',4,4',4''-pentahydroxy-5,5'-dicyclohexyl-TPM | 154.1 | 163 | 266 | 44 | 6,700 | 363,000 |
| 8. | 2,2',4,4',4''-pentahydroxy-5,5'-di-n-hexyl TPM | 154.5 | 165 | 266 | 38 | 9,400 | 308,000 |
| 9. | 2,2',4,4',4''-pentahydroxy-5,5'-didodecyl TPM | 210.5 | 200 | 266 | 16 | 8,800 | 235,000 |
| 10. | 4,4',4''-trihydroxy-1,1,1-triphenylethane | 159.0 | 171 | 260 | 45 | 8,200 | 457,000 |

TPM — triphenylmethane;
EEW — epoxide equivalent weight;
HDT — heat distortion temperature

EXAMPLE 6

Blends of the trisepoxide of leucaurin (TEL) and the diglycidyl ether of bisphenol A (DGEBA), epoxy equivalent weight of 172 to 176, and a curing agent were prepared. The blends were formed into test specimens and cured at 93° C. for 2 hours and then 232° C. for 15 hours. The results are in Table 5 below:

TABLE 5

| No. | Wt. % DGEBA | Wt. % TEL | Curing Agent | Parts Curing Agent/100 Parts Resin | Heat Distortion Temperature - °C. |
|---|---|---|---|---|---|
| 1. | 80 | 20 | MDA | 28.3 | 179 |
| 2. | 50 | 50 | MDA | 28.3 | 210 |
| 3. | 20 | 80 | MDA | 28.3 | 264 |
| 4. | 80 | 20 | PMDA MA | | 193 |
| 5. | 50 | 50 | PMDA MA | 13.3 | 247 |
| 6. | 20 | 80 | PMDA MA | 24.0 | 262 |
| 7. | 80 | 20 | PMDA MA | | 157 |
| 8. | 50 | 50 | PMDA MA | 13.3 | 226 |
| 9. | 20 | 80 | PMDA MA | 24.0 | 265 |

MDA — Methylene Dianiline
PMDA — Pyromellitic Dianhydride
MA — Maleic Anhydride

Other epoxides of this invention would give similar improvement in the high temperature characteristics of bisphenol A.

EXAMPLE 7

Blends of the trisepoxide of leucaurin (TEL), another resin (as specified below) and 1 part of metaphenylene diamine per hundred parts of resin were prepared, shaped and cured at 85° C. for 16 hours and 160° C. for another 16 hours. The results are in Table 6 below:

TABLE 6

| No. | Wt. % TEL | Other Epoxy Resin | Wt. % of Other Epoxy Resin | Heat Distortion Temperature - °C. | Flexural Strength(psi) |
|---|---|---|---|---|---|
| 1. | 100 | None | 0 | 265 | 14,100 |
| 2. | 75 | A | 25 | 204 | 18,200 |
| 3. | 50 | " | 50 | 198 | 21,000 |
| 4. | 75 | B | 25 | 198 | 16,000 |
| 5. | 50 | " | 50 | 193 | 21,500 |
| 6. | 0 | " | 100 | 153 | 32,600 |
| 7. | 75 | C | 25 | 197 | 15,200 |

TABLE 6-continued

| No. | Wt. % TEL | Other Epoxy Resin | Wt. % of Other Epoxy Resin | Heat Distortion Temperature - °C. | Flexural Strength(psi) |
|---|---|---|---|---|---|
| 8. | 50 | " | 50 | 182 | 17,700 |

A - Vinylcyclohexene diepoxide, distributed by Union Carbide Corporation under designation ERLA 4206.
B - Copolymer of ethylene glycol and mixed isomers of bis(2,3-epoxycyclopentyl) ether, distributed by Union Carbide Corporation under designation ERLA 4617.
C - Resorcinol diglycidyl ether, distributed by CIBA Corporation under designation ERE 1359.

EXAMPLE 8

Comparison of Epoxides Made from Leucaurin By Methods Disclosed in Prior Art and Herein In order to clearly demonstrate the superior qualities of the epoxides of the instant invention, the following experiments were carried out:

Four samples of the glycidyl ether of leucaurin were prepared according to different methods as follows, the identifying designations given being used throughout—

1. DEARBORN—The following method was used to duplicate as closely as possible the method of Dearborn in epoxidizing leucaurin, as taught in the aforementioned I & EC article. 583 Grams of epichlorohydrin, a 5-fold portion based upon the leucaurin to be employed, were placed in a two-liter, three-necked flask, fitted with a stirrer and thermometer. The flask contents were heated to 60°.

123 Grams of leucaurin, 1.262 equivalents (0.421 moles) were dissolved in 505 milliliters of aqueous 10 weight percent sodium hydroxide, thereby obtaining a dark red solution.

Vigorous stirring of the heated epichlorohydrin was begun, the sodium hydroxide-leucaurin solution was added very slowly, with continuous vigorous stirring. In advance, it had been expected that the exotherm of reaction would elevate the temperature of the flask contents by 10 degrees, to 70° or above, but no such exotherm occurred. External heating was applied to elevate the flask contents temperature to 70°, and stirring was continued along with addition of the solution of leucaurin and sodium hydroxide. A very small exotherm of reaction elevated the flask contents temperature to 74°.

The addition of the 628 grams of sodium hydroxide-leucaurin solution was completed in 50 minutes. Thereafter, heating with stirring was continued for an additional 90 minutes to attempt to carry the reaction to completion.

Reaction between sodium hydroxide and epichlorohydrin yielded sodium chloride. This brine solution was separated and the resulting product was washed with dilute sodium chloride solution that had been acidified with a small amount of acetic acid. The resulting product was then dried over anhydrous magnesium sulfate, and flask distilled under sub-atmospheric pressure to remove unreacted epichlorohydrin.

2. NEUMANN—Example 2 of British Pat. No. 875,811 was followed utilizing leucaurin as the starting phenolic.

3. SCHWARZER—Example 3 of U.S. Pat. No. 2,965,611 was followed utilizing leucaurin as the starting phenolic.

4. INVENTION—Example 3 of the instant specification was followed in preparing the epoxide of this invention for this comparison.

The four epoxides, made from the same starting materials but utilizing four different epoxidation methods, were then mixed with a stoichiometric amount (49.5 g./OH eq.) of methylene dianiline, shaped into test specimens, and cured for 2 hours at 100° C. and then 18 hours at 180° C.

The pertinent data determined from both the cured and uncured resins is in Table 7 below:

TABLE 7

| Epoxide | Ep. Eq.Wt. Found[1] | Ep. Funct. Found[2] | Avg. Mol. Wt.[3] | H.D.T. °C.[4] | Flex Strength (psi) | Flex Modulus (psi) |
|---|---|---|---|---|---|---|
| Dearborn | 294 | 2.0 | 588 | 147 | 8,700 | 492,000 |
| Neumann | 432 | 1.3 | 562 —[5] | — | — | — |
| Schwarzer | 218 | 2.1 | 458 | 193 | 12,100 | 520,000 |
| Invention | 156 | 3.1 | 484 | 350 | 12,000 | 460,000 |

[1]Epoxy Equivalent Weight (Theory = 153)
[2]Epoxide Functionality (Theory 3.0) = (Avg. Mol. Wt. found) ÷ (Av. EEW found)
[3]Average molecular weight found
[4]Heat Distortion Temperature
[5]The sample bubbled and foamed during cure. Further tests were impossible.

EXAMPLE 9

In order to illustrate the effectiveness of small changes in the relative concentration of the epoxides of this invention when blended with other epoxides, the following experiments were conducted.

The indicated weight %'s of the trisepoxide of leucaurin (TEL) and the diglycidyl ether of dihydroxy triphenyl 1,1,1-ethane (DTEE) was admixed with the stoichiometric amount of metaphenylene diamine, and cured at 85° C. for 16 hours and 160° C. for 16 hours. The resuls are in Table 8 below:

TABLE 8

| No. | Wt. % TEL | Wt. % DTEE | Barcol Hardness | Heat Distortion Temperature-°C. | Flexural Strength (psi) |
|---|---|---|---|---|---|
| 1 | 95 | 5 | 47 | 263 | 12,800 |
| 2 | 90 | 10 | 49 | 245 | 12,300 |
| 3 | 85 | 15 | 47 | 222 | 11,800 |
| 4 | 80 | 20 | 47 | 210 | 12,900 |
| 5 | 70 | 30 | 45 | 201 | 13,500 |
| 6 | 50 | 50 | 45 | 190 | 13,400 |

EXAMPLE 10

To further exemplify the enhancing effect which the addition of small amounts of the resins of this invention have on the high temperature properties of other resins, the following experiments were conducted.

The indicated weight % of TEL, similar to that in Example 8, was admixed with the diglycidyl ether of bisphenol A (DGEBA). Stoichiometric amounts of methylene dianiline were used as the curing agent, the curing conditions being 2 hours at 100° C. and 18 hours at 180° C. The results are in Table 9 below:

TABLE 9

| No. | Wt. % TEL | Wt. % DGEBA | Heat Distortion* Temperature-°C. |
|---|---|---|---|
| 1 | 0 | 100 | 160 |
| 2 | 10 | 90 | 177 |
| 3 | 20 | 80 | 198 |
| 4 | 50 | 50 | 219 |
| 5 | 80 | 20 | 331 |
| 6 | 90 | 10 | 339 |

*Determined by thermal mechanical analysis, as discussed in Perkin-Elmer Industrial News 20, No. 4 (1970), pages 6–7, as adapted to duPont Thermal Mechanical Analyzer instrument utilizing same sample size (0.3" × 0.2" × 0.02").

While the monomeric tris (etc.) epoxides are the preferred products of the present invention for uses requiring the highest Heat Distortion Temperatures, epoxidation products of higher molecular weights which consist predominantly of the oligomers are also highly useful. The oligomeric products possess similar high heat distortion properties and have the added advantage of being obtainable in solid form, rather than the generally semi-solid or viscous liquid forms of the monomeric epoxidation products.

The "catalytic" epoxidation process (i.e., utilizing a coupling catalyst) described earilier herein is suitable for making products in which the oligomers predominate but is best suited for making products which consist predominantly or almost entirely of the monomers. Another epoxidation process has been devised which is distinctly superior for the production of oligomers (but is also well adapted for preparation of predominantly monomeric products). This process differs in that the coupling step is carried out essentially in the absence of coupling catalysts and solvents and the dehydrohalogenation step is carried out in the presence of solvents having the characteristics of methylethyl ketone/toluene mixtures. The net effect of these differences is to substantially reduce the amount of undesirably high molecular weight and/or insoluble products co-formed when the really low epihalohydrin/phenolic hydroxyl ratios essential to maximal oligomer production are employed. Apparently, further growth of oligomers having m values (see Formula II) of about 2 to 3 is considerably retarded and side reactions leading to production of insoluble products are largely inhibited.

In the latter process, products containing more or less of oligomers can be produced by using epihalohydrin to phenolic hydroxyl ratios of from about 1 to about 10. At the lower end of this range (preferably at a ratio of from about 1.1 to 1.5), the product will consist almost completely or at least predominantly of oligomers. At the upper end of the range, preferably from about 5 to about 10, both the content and average molecular weight of the oligomers present in the product will be relatively low. Even higher ratios may be used when products consisting predominantly or almost entirely of monomeric epoxides are desired, but with so little further advantage as to be generally not worth the additional processing required to recover (and recycle) the greater excess of the epihalohydrin. For the latter type of products, a ratio of from about 6 to about 9 is preferred; in the specific case of trihydroxy triphenyl methanes, a ratio of about 8.5 appears to be optimal.

In the preparation of largely monomeric products, it is preferred but not indispensible to use a mixture of methylethyl ketone ("MEK") and toluene as the reaction medium (in the dehydrohalogenation step). Any solvent or solvent mixture which exhibits the foregoing characteristics to a substantial extent and is otherwise suitable (for the subsequent stability and recoverability of the desired product, etc.) may be used. However, for the preparation of largely oligomeric products, MEK/toluene mixtures or solvent systems having essentially the same growth-retarding and side-reaction inhibiting characteristics should be used and are highly preferred. For oligomeric products containing very little of monomeric epoxides, the use of MEK/toluene is considered a necessity.

The solvent to triphenol ratio is generally not sharply critical but will usually be at least 50 parts by weight per 100 parts of the polypenol. The optimum solvent to resin ratio for the preparation of any specific product can readily be determined without undue experimentation but will generally be within the range of from about 70 to about 100 parts by weight of the solvent per 100 parts of the phenolic starting material. Higher ratios may be suitable but will tend to decrease the compatibility of the aqueous and organic reactants. Thus ratios in excess of about 125 to 100 will generally not be advantageous.

The MEK to toluene ratio found most suitable for preparing oligomeric epoxides from 2,4′,4″-tri- or 4,4′,4″-tris(hydroxyphenyl)methanes is about 3 parts by weight of MEk per part of toluene. However, it is believed that the benefits of this solvent combination can be substantially realized over the entire range of from about 2 to about 4 parts of MEK per part of toluene.

For the preparation of predominantly monomeric epoxides, the MEK to toluene ratio is less critical and ratios in the range of from about 1 to about 5 parts of MEK per part of toluene are belived suitable. Correspondingly, the characteristics required for other suitable solvents or solvent mixtures are those exhibited over the latter range by MEK/toluene mixtures. Exemplary of other solvent systems which may have such characteristics are diethyl ketone/toluene, diethylketone/xylenes and cyclohexanone/toluene or methylisobutyl ketone alone.

The process of the present invention may then be broadly defined as the method for preparing epoxides of the foregoing Formulas I and II which comprises (1) reacting a polyhydroxy triphenyl alkane of Formula A with at least 1 mole, per equivalent of phenolic hydroxyl, of an epihalohydrin of Formula B, essentially in the absence of coupling catalysts and solvents and in the presence of more than 1 and up to about 3 equivalents per phenolic hydroxyl, of an aqueous base; (2) adding up to about 2 equivalents more of aqueous base and a solvent (or solvent system) having the characteristics of a mixture of methylethyl ketone and toluene; (3) dehydrohalogenating the product of step (1) with the base present after step (2), and (4) recovering said epoxide.

The most preferred embodiment of the process aspect of the invention is illustrated in the following example, wherein a predominantly oligomeric product is made.

EXAMPLE 11

Epichlorohydrin (114.1 grams, 1.23 moles) was added to 100 grams (0.342 moles) of 2,4′,4″-trihydroxytriphenyl methane (an equivalent ratio of $(1.23/(0.342\times 3))=1.2:1$). The resulting mixture was heated moderately and stirred until the starting material dissolved in the epichlorohydrin. After elevating the temperature to about 90° C., the rate of stirring was increased and 51.5 grams (1.29 moles) of NaOH $(1.29/(0.342\times 3))=1.25$ moles per phenolic hydroxyl in the starting material) was addes portionwise, as a 25% aqueous solution, over a one-hour period. When addition of about 60% of the NaOH solution was completed, 100 ml (80 grams) of a 3:1 mixture of methylethylketone and toluene was added to the reaction mixture and the NaOH addition continued. Following the solvent mixture addition, the temperature of the reaction mixture decreased from about 100 to about 85° C. After the NaOH addition was completed, the reaction mixture was heated with stirring at 80°-85° C. for another 90 minutes and then mixed with another 200 ml (160 grams) portion of the solvent mixture and 50 ml of water. A concentrated brine, which formed at the bottom of the mixture, was separated therefrom. Solvent was then stripped from the reaction mixture (under 20-25 inches of vacuum), with final removal of volatiles being done by steam stripping under vacuum. As a result of these operations, a clear, amber, hard and brittle resin with an Epoxy Equivalent Weight (EEW) of about 215-240, a melt viscosity of 500-1000 centistokes at 150° C., and Duran softening point of 80°-85° C. was obtained. Based on the EEW, the average epoxy functionality appears to be that of a dimer (theoretical EEW=216), e.g., epoxide functionality of about 4. However, from the results of GPC (Gel Permeation Chromatographic) analysis, it appears the monomer and dimer each comprise about 20-25% of the product while the trimers and tetramers together comprise about 50-60%. Various 2 gram samples of the resin were mixed with stoichiometric amounts of a curing agent (methylene dianiline) and cured for 2 hours at 90° C., 4 hours at 165° C. and 16 hours at 200° C. Heat distortion temperatures were determined by the known TMA method and found to range from about 245°-253° C. Similar TMA tests on the cured tris-epoxide of leucaurin of Example 3 were found to be about 246° C.

When the foregoing preparation is carried out in essentially the same manner otherwise but at an epi to phenolic hydroxyl ratio of 1.5, the EEW of the product drops to about 205, the monomeric epoxide content rises to about 30%, and the viscosity of the product decreases accordingly to about 400 c.s.

What is claimed is:

1. The epoxidation product of a phenolic compound of the formula

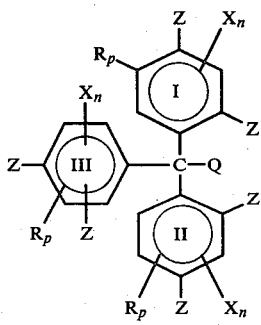

wherein:
Q is H or an alkyl group of from 1 to about 10 carbon atoms;
each R independently represents an alkyl group of from 1 to about 12 carbon atoms, phenyl or cycloalkyl of from 3 to about 6 carbon atoms;
each Z independently represents H or OH, with the proviso that at least one Z group on each of Rings I, II and III is OH;
each X independently represents bromo, chloro or nitro;
each p independently is 0, 1 or 2, each n independently is 0, 1, or 2, the sum of n+p for each ring being 0, 1, 2 or 3 when each Z is other than hydrogen,
and an epihalohydrin of the formula:

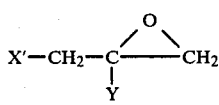

wherein X' is Cl or Br and Y is H or —CH$_3$;
said epoxidation product having an average epoxide functionality of from about 2.5 to about 6.0, or at least about 70% of theoretical for the number of available hydroxyls, whichever is greater.

2. The epoxidation product of claim 1 wherein, in the phenolic compound, each n is zero.

3. The epoxidation product of claim 1 wherein, in the phenolic compound, each p is zero.

4. The epoxidation product of claim 1 wherein, in the phenolic compound, each n and each p is zero.

5. The epoxidation product of claim 1 wherein, in the phenolic compound, one Z on Ring III is H.

6. The epoxidation product of claim 1 wherein, in the phenolic compound one Z is H on each of rings I, II and III.

7. The epoxidation product of claim 1 wherein, in the phenolic compound, Q is H.

8. The epoxidation product of claim 2 wherein, in the phenolic compound, Q is H.

9. The epoxidation product of claim 3 wherein, in the phenolic compound, Q is H.

10. The epoxidation product of claim 4 wherein, in the phenolic compound, Q is H.

11. The epoxidation product fo claim 5 wherein, in the phenolic compound, Q is H.

12. The epoxidation product of claim 6 wherein, in the phenolic compound, Q is H.

13. The product of claim 10 wherein, in said phenolic compound, one Z in ech of rings I, II and III is H.

14. The epoxidation product of claim 1, 2, 3, 4, 5, 6, 7, 8, 9, 10, 11, 12 or 13 which is predominantly monomeric and has an epoxide functionality of from about 2.5 to about 5.

15. The epoxidation product of claim 13 which has an epoxide functionality of from about 2.5 to about 5.

16. The epoxidation product of claim 13 which is predominantly monomeric and has an epoxide functionality of from about 2.8 to about 3.2.

17. The epoxidation product of claim 16 wherein said phenolic compound is tris-(4-hydroxyphenyl)methane.

18. The epoxidation product of claim 16 wherein said phenolic compound is 2,4',4''-trihydroxytriphenylmethane.

19. The product of claim 17 which is tris-(4-glycidyloxyphenyl)methane.

20. The product of claim 18 which is 2,4',4''-tri(-glycidyloxy)triphenylmethane.

21. The epoxidation product of claim 1, 2, 3, 4, 5, 6, 7, 8, 9, 10, 11, 12 or 13 which is predominantly oligomeric and has an epoxide functionality of from about 3.5 up to the value of $f_E$ which satisfies the equality $$f_E = \frac{(N - 2)(M_o - 2M_p - (2N - 1)M_G + 2N - 1)}{M_p + (N - 1)(M_G - 1)} + 2(N - 1)$$

wherein N is the number of available phenolic hydroxyls in the polyphenol of said formula (A), $M_o$ is the average molecular weight of said product, $M_p$ is the molecular weight of the polyphenol and $M_G$ is the molecular weight of the glycidyl portion of the epihalohydrin of said formula (B).

22. The epoxidation product of claim 13 which has a viscosity of from about 8500 to about 30,000 centistokes or more at about 50° C.

23. The cured epoxidation product of claim 1.

24. The product of claim 19, cured with methylene dianiline and having a heat distortion temperature of from about 246° to about 350° C.

25. A blend of epoxides comprising at least 5 weight % of the epoxidation product of claim 1, the remainder comprising a mono- or a poly-functional epoxide, or mixtures thereof.

26. The blend of claim 25 in which said product is predominantly monomeric and has an average epoxide functionality of from about 2.8 to about 3.2.

27. The cured epoxy blend of claim 25.

28. The cured epoxy blend of claim 26.

29. The product of claim 10 which is a clear, amber, hard and brittle, predominantly oligomeric resin having an EEW of from about 205 to about 240, a melt viscosity of from about 400 to about 1000 centistokes at 150° C. and a Duran softening point of from about 80 to about 85° C., and wherein said phenolic compound is 2,4',4''-(trihydroxy)triphenyl methane or tris-(4-hydroxyphenyl)methane.

30. The product of claim 29, cured with methylene dianiline and having a heat distortion temperature of from about 245° to about 253° C.

31. The product of claim 29 having an average epoxide functionality of about 4.

32. The method of preparing an epoxidation product of claim 1 which comprises
(1) reacting a tri(hydroxyphenyl)alkane of the formula

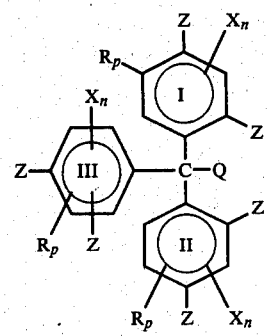 (A)

wherein:
Q is H or an alkyl group of from 1 to about 10 carbon atoms;
each R independently represents an alkyl group of from 1 to about 12 carbon atoms, phenyl or cycloalkyl of from 3 to about 6 carbon atoms;
each Z independently represents H or OH, with the proviso that at least one Z group on each of Rings I, II and III is OH;
each X independently represents bromo, chloro or nitro;
each p independently is 0, 1 or 2, each n independently is 0, 1, or 2, the sum of n+p for each ring being 0, 1, 2 or 3 when each Z is other than hydrogen,
with at least one molecular proportion, per phenolic hydroxyl in said alkane, of an epihalohydrin of the formula

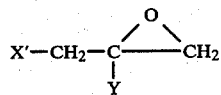 (B)

wherein X' is Cl or Br and Y is H or —$CH_3$;
in the presence of more than 1 and up to about 3 equivalents per phenolic hydroxyl of and aqueous base and essentially in the absence of coupling catalysts and solvents, then (2) adding a solvent having the characteristics of a methylethylketone/toluene mixture and up to about 2 more equivalents of aqueous base and continuing the reaction until the content of hydrolyzeable chloride in the reaction product has dropped to an acceptably low value, and then (3) recovering said product.

33. The method of claim 32 wherein said phenolic compound is a tri(hydroxyphenyl)methane, the total amount of said base employed is such as to provide about 1.25 equivalents of hydroxyl per equivalent of phenolic hydroxyl, and said reaction is carried out as follows:

(a) over a period of about an hour, the base is added incrementally to a hot, agitated solution consisting essentially of said phenolic compound and from about 1.2 to 1.5 molecular proportions, per phenolic hydroxyl, of epichlorohydrin, (b) when about 60% of said base has been added, about 80 parts by weight of said solvent mixture per 100 parts of said alkane is added, the base addition being continued, (c) when the base addition is complete, the resultant reaction mixture is agitated at a temperature of from about 80 to about 85° C. for an additional period of about 1.5 hours, and then (d) about 180 parts more of said solvent mixture and about 45 parts of water are mixed into the reaction mixture, resulting in separation of a brine phase, and (e) the brine phase is removed and the organic phase stripped under reduced pressure and finally with steam, thereby producing a clear, brittle, amber, predominantly dimeric resin with an epoxide equivalent weight of from about 205 to about 240, a melt viscosity of from about 500 to about 1000 centistokes at 150° C., a Duran softening point of from about 80° to about 85° C. and an average epoxide functionality of about 4.

* * * * *